United States Patent [19]

Peterson et al.

[11] 3,962,301
[45] June 8, 1976

[54] PREPARATION OF ALKYLENE DIISOCYANATES

[75] Inventors: Laurence I. Peterson, Doylestown, Pa.; Michael J. VanEyck, Midland, Mich.

[73] Assignee: The Dow Chemical Company, Midland, Mich.

[22] Filed: Mar. 5, 1975

[21] Appl. No.: 555,481

[52] U.S. Cl. .................... 260/453 P; 260/239 BC;
    260/251 R; 260/309.7
[51] Int. Cl.² .................................... C07C 118/00
[58] Field of Search ............................ 260/453 P

[56] References Cited
UNITED STATES PATENTS
3,275,618  9/1966  Tilley et al. .................... 260/453 X Primary Examiner—Lewis Gotts
Assistant Examiner—Dolph H. Torrence
Attorney, Agent, or Firm—David H. Fifield

[57] ABSTRACT

Alkylene diisocyanates of the formula OCN-R-NCO are prepared by heating a compound of the formula

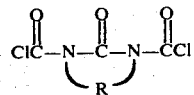

at a temperature of about 200° to about 500°C. wherein —R— is dimethylene, trimethylene or tetramethylene which may bear lower alkyl substituents. For example, ethylene diisocyanate is prepared by heating ethylene urea N,N'-dicarbonyl chloride at about 350°C.

9 Claims, No Drawings

PREPARATION OF ALKYLENE DIISOCYANATES

BACKGROUND OF THE INVENTION

The invention comprises a process for preparing alkylene diisocyanates by heating N,N'-alkylene urea-N,N'-dicarbonyl chlorides at a temperature sufficient to cause dephosgenation.

Aliphatic diisocyanates have generally been prepared by an azide degradation process known as the Curtius method. Tilley et al. in U.S. Pat. No. 3,275,618 (1966) describe the preparation of alkylene diisocyanates by pyrolysis of N,N'-alkylene allophanyl chlorides.

SUMMARY OF THE INVENTION

The invention is a process for the production of alkylene diisocyanates comprising heating, at a temperature sufficient to cause dephosgenation, a compound represented by the formula (II)

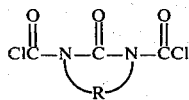

wherein —R— is dimethylene, trimethylene or tetramethylene which may bear from 1 to 8 lower alkyl groups of from 1 to 3 carbon atoms each. Produced by this process are compounds represented by the formula (I) OCN-R-NCO, wherein —R— is as defined above, which may be condensed with polyols, polythiols, or other active hydrogen functional groups to prepare polymers, i.e. urethanes and the like. These polymers are used to form films, foams, and other useful products. The reaction process is suitably carried out at a temperature of about 200° to about 500°C. and preferably at a temperature of about 250° to about 400°C. The alkylene moiety —R— is preferably dimethylene or trimethylene which bears 1 or 2 methyl groups and most preferably is 1,2-ethylene; 1,2-propylene; or 1,3-propylene.

DETAILED DESCRIPTION OF THE INVENTION

Preparation of Precursors

The starting materials of formula (II)

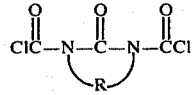

are prepared by contacting, in a phosgene and HCl resistant vessel, a N,N'-alkylene urea represented by the formula (III)

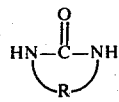

with phosgene in the phosgene: (III) molar ratio of at least 2:1 at a temperature of about 0°–250°C. It appears that the reaction of phosgene with (III) takes place in a stepwise fashion; the first —COCl radical reacting with one nitrogen atom at a temperature above about 0°C. and the second radical reacting at above about 100°C. Alternatively, phosgene and (III) are mixed at below the reaction temperature in at least a 2:1 molar ratio and the temperature is raised to above about 100°C., preferably to between about 120° and 160°C.

For example, (III) may be ethylene urea, propylene urea (1,2-propylene urea), trimethylene urea (1,3-propylene urea), tetramethylene urea or the like. Other N,N'-alkylene ureas may be produced by the method of Schweitzer in *J. Org. Chem.* 15:471 (1950) by contacting a properly substituted alkylene diamine, of the desired —R—, with urea. They may also be produced by contacting phosgene and an alkylene diamine of the formula $H_2N$-R-$NH_2$ at between about −30° and about 200°C., preferably at about 25° to 50°C., in a phosgene:alkylene diamine molar ratio of about 3 or greater. In this manner, the starting material of formula (II) with the linking —R— portion bearing lower alkyl substituents such as methyl, ethyl, propyl, etc. may be prepared from the corresponding N,N'-alkylene urea or alkylene diamine of which the —R— portion bears the desired substitution.

The precursors are preferably prepared in an inert solvent, having no active hydrogens, such as nitrobenzenes, chlorobenzenes, chlorotoluenes and the like. They are generally recovered by boiling off excess solvent and recrystallizing the generally solid precursors from a suitable solvent such as benzene.

Preferred in the invention are starting materials of the formula (II) wherein —R— is dimethylene or trimethylene which may bear up to 2 methyl groups. Most preferred are compounds wherein —R— is 1,2-ethylene; 1,2-propylene; or 1,3-propylene. Other representative compounds are those of formula (II) where —R— is: —$CH_2CH_2CH_2CH_2$—; —$CH_2C$(—$CH_3$)$_2C$-$H_2$—; —CH(—$CH_3$)CH(—$CH_3$)—; —($CH_2C$-H(—$CH_3$)$CH_2$—; —CH(—$CH_3$)$CH_2$CH(—$CH_3$)—; —CH(—$C_2H_5$)$CH_2$—; —$CH_2$CH(—$C_3H_7$)$CH_2$— and the like.

Dephosgenation Temperature

The diisocyanates of the formula (I) OCN-R-NCO are prepared by heating the N,N'-alkylene urea -N,N'-dicarbonyl chlorides of formula (II) to a temperature sufficient to cause dephosgenation of compound (II). By dephosgenation is meant that the compound of formula (II) releases up to about an equal molar amount of "phosgene" by thermal pyrolysis. The word dephosgenation as used herein describes the pyrolysis of compounds of formula (II) which produces an equivalent quantity of chlorine, carbon, and oxygen for the amount of alkylene diisocyanate produced.

Said pyrolysis may be represented schematically by the equation:

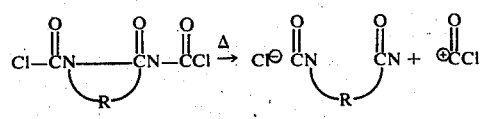

It is not known whether the pyrolysis actually proceeds through the mechanism shown in the equation and we do not intend to be limited thereby. In fact, it is believed that phosgene, if produced, to some degree disproportionates at higher temperatures into carbon dioxide and carbon tetrachloride. At lower temperatures some phosgene may be recovered and recycled if desired.

Dephosgenation occurs when the compounds of formula (II) are heated at a temperature of between about 200°–500°C. Dephosgenation of (II) is preferably carried out at a temperature of about 250° to 400°C.

Process Conditions

The dephosgenation reaction of the invention may be carried out in any reactor vessel suitable for retaining and collecting the gaseous product and byproducts. Said reactor vessel may suitably be composed of materials that are inert to phosgene and hydrogen chloride such as high silica glass or stainless steel. The reactor vessel may be heated by any suitable heat source capable of maintaining a temperature of between about 200° and 500°C. in the reaction vessel. Suitable heat sources include electric heating coils, electric furnaces, molten salt baths, and the like.

Of primary concern is the maintenance of good heat transfer from the heat source to reactant (II). This may be achieved by using a narrow bore, hot tube reactor. Such a hot tube may suitably be packed with materials such as silica chips or rings, metallic pellets of aluminum, copper, platinum, palladium and or pellets of silicone carbide and the like. Dephosgenation may also be carried out in a reactor vessel of relatively large volume which has been packed with suitable solid materials as mentioned above or which is filled with a liquid heat transfer medium such as mineral oil, silicone fluid, mercury or with other materials which remain in the solid or liquid phase at the dephosgenation temperature and which are good heat transfer media.

Reactant (II) is suitably fed to the reaction vessel as a liquid solution which is brought into direct contact with the packing or a liquid heat transfer medium in the reaction vessel or alternatively into direct contact with the vessel walls. This may be accomplished by directing a liquid solution of reactant (II) under the surface of a liquid heat transfer medium within the vessel; by direct contact of the reactant solution with the surface of the heat transfer material, or packing; or by passing reactant solution through a nozzle with an inert gas such as nitrogen or argon and directing the spray from said nozzle on the surface of the packing or liquid heat transfer medium or onto the walls of the reaction vessel. It is also advantageous to sweep the reaction vessel with an inert diluent gas such as nitrogen or argon which will serve to remove the gaseous alkylene diisocyanate and byproducts thereby improving the efficiency of the reaction. Reactant (II) may also be preheated to about 130° to 200°C. prior to its introduction into the reaction vessel.

The compounds of formula (II) are generally solids at the dephosgenation temperature and are preferably dissolved in a suitable inert solvent prior to their introduction into the reaction vessel. Suitable solvents are those having no active hydrogen groups and being stable, inert liquids under reaction conditions. Aromatic liquids such as chlorobenzenes, benzene and nitrobenzene have been found suitable, as has sulfolane. Nitrobenzene is a good solvent for reactant (II) but co-distills at about the same temperature as the products making recovery somewhat more difficult. Reactant (II) is therefore dissolved in the chosen solvent to whatever extent possible, depending on the solvent. Ordinarily between 5–20% of reactant (II) by weight may be dissolved in the inert solvent.

As mentioned above, gaseous alkylene diisocyanate and reaction byproducts are suitably flushed from the reaction vessel by passing a stream of inert gas such as nitrogen or argon through the reaction vessel. These gases may exit the reaction vessel at a point suitably removed from the point where the reactant (II) is introduced. This gaseous mixture is then passed through a cold trap wherein the alkylene diisocyanate is condensed and collected. It may be separated from other condensibles by fractionation means. The inert gas-phosgene mixture may be recovered or disposed of by any suitable means.

The reaction may be carried out at the autogenous pressure generated by the gaseous products or under mild pressures produced by the introduction of the inert diluent gas used to sweep the products from the reaction vessel. A mild vacuum may be pulled on the exit from the reaction vessel if desired.

SPECIFIC EMBODIMENTS OF THE INVENTION

Example 1: Preparation of Reactant (II)

About 50 ml. of preheated (180°C.) 2.85 molar solution of ethylene urea in nitrobenzene was added to an agitated, refluxing solution of 500 ml. of nitrobenzene at 150°C. which had been saturated with phosgene. The nitrobenzene-phosgene mixture contained more than the stoichiometric amount of phosgene needed to react with both amido groups of the ethylene urea reactant.

The temperature of the mixture was thereafter maintained at about 150°C. and 1 mg. samples were withdrawn at intervals of 3, 5 and 50 minutes after the initial addition of ethylene urea. These samples were purged with nitrogen, while hot, to remove any unreacted phosgene. Infrared spectroscopy showed complete conversion of ethylene urea to the monocarbonyl chloride in the 3 minute sample and the 5 minute sample gave a spectrum identical to that of the 3 minute sample. The 50 minute sample's spectrum indicated essentially complete conversion of ethylene urea and its monocarbonyl chloride to the dicarbonyl chloride as evidenced by the sample's characteristic spectrum with bands at about 1830, 1850 and 1725 cm.$^{-1}$, in order of decreasing intensity respectively. The characteristic band at about 3420 cm.$^{-1}$, representing the amido nitrogen of the monocarbonyl chloride, was only slightly visible while no band was discernible at about 3460 cm.$^{-1}$ where the absorption band characterizing ethylene urea's two amido nitrogens is normally found.

The crude product was recovered as an orange-brown solid from which the pure N,N'-dicarbonyl chloride of ethylene urea was obtained by recrystallization from benzene at about 10°C. This pure product, an off-white amorphous solid, had a melting point of 92°–94°C. IR and NMR analyses confirmed the structure. Elemental analysis was as follows:

|  | C | H | N | Cl | (wt. %) |
| --- | --- | --- | --- | --- | --- |
| Calculated: | 28.5 | 1.9 | 13.3 | 33.6 |  |
| Observed: | 28.7 | 2.1 | 13.9 | 31.9 |  |

Ethylene urea-N,N'-dicarbonyl chloride was also produced in this manner in sulfolane, chlorobenzene and trichlorobenzene at temperatures from about 50°–160°C.

Example 2: Dephosgenation of Ethylene Urea N,N'-Dicarbonyl Chloride

Ethylene urea N,N'-dicarbonyl chloride (hereinafter EUDC) which had been produced and purified in a manner similar to that described in Example 1 was dissolved in sulfolane to make about 93 grams of a 20% solution, by weight. This solution was placed in a flask which was attached to a distillation apparatus and the pot was heated to about 225°C. under 80 mm. vacuum. Ethylene diisocyanate (hereinafter EDI) and sulfolane co-distilled at a head temperature of about 200°C. EDI was identified in the product by IR and NMR spectroscopy.

Example 3: Dephosgenation in a Packed Tube

A 0.4 molar solution of EUDC in o-dichlorobenzene was fed dropwise into a heated, 1 inch by 24 inch Vycor high silica column which was packed with ¼ inch ceramic saddles. The ceramic saddle reaction zone was heated to about 500°C. by an electric furnace and a stream of nitrogen was passed downward through the column concurrently with the feed at about atmospheric pressure. Some charring occurred on the upper portion of the packing and a 22% yield of EDI, based on 100% EUDC conversion, was recovered. The product was identified by IR and NMR spectroscopy.

Example 4: Stainless Steel Packed Column

A number of runs were conducted in various solvents in a two stage apparatus which was made of a wide, vaporizer column, containing approximately 875 ml. of stainless steel rings as packing, which was connected to a second, narrower reaction column also packed with stainless steel rings having a volume of about 125 ml. The two portions of the apparatus were heated in an electric furnace. A reaction mixture of about equal molar quantities of the monocarbonyl chloride of ethylene urea and EUDC (an unpurified mixture from the ethylene urea-phosgene prep) in nitrobenzene or in chlorobenzene was fed to the column from a dropping funnel by dropping directly on the vaporizer packing. A stream of dry nitrogen gas was passed through both the vaporizer and reactor columns at a rate of about 45 to 200 moles per hour. The vaporizer temperature varied between about 325° and about 450°C. and the temperature of the second reaction column ranged from about 275° to about 470°C. the conversion of EUDC ranged from about 75% to 100% and the yield of the EDI based on EUDC converted ran from about 10% up to about 55% on the average. Best results were obtained when the vaporizer temperature was about 445°C. and the second reaction vessel about 400°C. with about equal molar amounts of the monocarbonyl and the dicarbonyl chloride of ethylene urea in chlorobenzene being fed at a rate of about 2 moles of the dicarbonyl chloride per hour and nitrogen diluent being passed at about 92 moles per hour.

About a 1:3 molar mixture of the mono- and dicarbonyl chloride of ethylene urea respectively, in benzene solution, was heated to between 350° to 450°C. and 355° to 465°C., vaporizer and reactor respectively, with nitrogen gas being passed at about 200 moles per hour. 100% Conversion of EUDC and about 24% yield of EDI, based on EUDC converted, was obtained as measured by IR analysis of one hour product samples. The total residence time of the reaction mixture in the two reaction chambers ranged from about 4 to 42 seconds.

Example 5: Mineral Oil Heat Transfer Medium

A number of runs were made in a round bottom two liter flask which contained about 1200 ml. of white mineral oil. The feed was a benzene solution containing between about 5 and 10% by weight of EUDC and also small amounts of the monocarbonyl chloride of ethylene urea (hereafter EUC). This feed was introduced to the reaction vessel by a tube which discharged the solution under the surface of the mineral oil. In most instances, dry nitrogen gas was also swept through this tube, out the exit at the top of the flask and through a water cooled condenser into a cold trap where the product was recovered. Conversion of EUDC was 100% in all instances. In several instances, suspended powdered aluminum metal or powdered copper metal was added to the mineral oil. Each run proceeded for 60 minutes. Analyses of the products recovered from the cold trap were by IR spectroscopy. The yields of EDI are based on the EUDC converted and results are reported below in Table I.

TABLE I

| Run No. | $\phi H$ Fed (g/hr) | EUDC (wt% in $\phi H$) | EUC (wt% in $\phi H$) | $N_2$ Fed (l/hr) | Temp. of Oil (°C.) | EDI Yield (wt%) | Comments |
|---|---|---|---|---|---|---|---|
| 1 | 25 | 11.2 | 2.5 | —+ | 275 | 17.7 | |
| 2 | " | " | " | — | 322 | 35.3 | |
| 3 | 30 | " | " | — | 333 | 28.8 | Cu added to oil |
| 4–5 | 27–28 | " | " | 179 | 350 | 27.6 | |
| 6 | 28 | " | " | " | 333 | 29.1 | 5–10% by wt. Al added to oil |
| 7 | 24 | 10.0 | 2.6 | " | " | 47.8 | " |
| 8 | 53 | " | " | " | " | 63.2 | " |
| 9–12 | 50–54 | " | " | " | 335 | 22–29 | |
| 13 | 51 | 10.3 | 2.7 | " | 385 | 18.3 | |
| 14–15 | 53–54 | 10.0 | 2.6 | 90 | 335 | 23–45 | |
| 16–18 | 53–54 | " | " | 45 | " | 20–21 | |
| 19–20 | 45–50 | 5.2 | 1.2 | " | " | 53–56 | |
| 21 | 96 | " | " | " | " | 57.4 | |
| 22 | 110 | " | " | " | " | 50.8 | |
| 23–24 | 42–43 | " | " | " | " | 55–62 | |
| 25 | 62 | " | " | 27 | " | 33.6 | |
| 26–29 | 61–62 | 5.1 | " | " | " | 32–52 | |
| 30 | 64 | 4.8 | 1.1 | " | " | 44.2 | |
| 31 | 110 | " | " | " | " | 57.0 | |
| 32 | 134 | " | " | " | " | 58.2 | |
| 33 | 298 | " | " | " | " | 48.4 | |
| 34 | 322 | " | " | " | " | 48.3 | |

UNITED STATES PATENT AND TRADEMARK OFFICE
CERTIFICATE OF CORRECTION

PATENT NO. : 3,962,301
DATED : June 8, 1976
INVENTOR(S) : Laurence I. Peterson and Michael J. VanEyck It is certified that error appears in the above-identified patent and that said Letters Patent are hereby corrected as shown below:

Column 2, line 60, the formula should read:

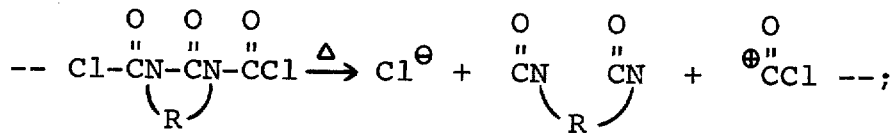

Column 2, line 68, after "temperatures" insert a comma --,--.

Signed and Sealed this

Twenty-first Day of September 1976

[SEAL]

Attest:

RUTH C. MASON
Attesting Officer

C. MARSHALL DANN
Commissioner of Patents and Trademarks